US008085399B2

United States Patent
Adams et al.

(10) Patent No.: US 8,085,399 B2
(45) Date of Patent: Dec. 27, 2011

(54) SYSTEMS AND METHODS FOR A MULTIPLE ANGLE LIGHT SCATTERING (MALS) INSTRUMENT HAVING TWO-DIMENSIONAL DETECTOR ARRAY

(75) Inventors: John A. Adams, Escondido, CA (US); Scott H. Bloom, Encinitas, CA (US); Victor J. Chan, San Diego, CA (US); Kristina M. Crousore, Oceanside, CA (US); Joseph S. Gottlieb, Escondido, CA (US); Oscar Hemberg, La Jolla, CA (US); John J. Lyon, San Marcos, CA (US); Brett A. Spivey, Carlsbad, CA (US)

(73) Assignee: JMAR LLC, San Diego, CA (US)

( * ) Notice: Subject to any disclaimer, the term of this patent is extended or adjusted under 35 U.S.C. 154(b) by 0 days.

(21) Appl. No.: 12/534,780

(22) Filed: Aug. 3, 2009

(65) Prior Publication Data

US 2010/0027007 A1     Feb. 4, 2010

Related U.S. Application Data

(63) Continuation of application No. 11/453,278, filed on Jun. 13, 2006, now Pat. No. 7,616,311, which is a continuation-in-part of application No. 11/381,346, filed on May 2, 2006, now Pat. No. 7,564,551, which is a continuation-in-part of application No. 11/231,350, filed on Sep. 19, 2005, now Pat. No. 7,532,327.

(60) Provisional application No. 60/690,535, filed on Jun. 13, 2005, provisional application No. 60/676,730, filed on May 2, 2005.

(51) Int. Cl.
*G01N 21/00* (2006.01)
(52) U.S. Cl. ...................................................... 356/338
(58) Field of Classification Search ........... 356/338–343
See application file for complete search history.

(56) References Cited

U.S. PATENT DOCUMENTS 3,871,769 A    3/1975    Engel et al.
(Continued)

FOREIGN PATENT DOCUMENTS

GB                2044445 A         10/1980
(Continued)

OTHER PUBLICATIONS

PCT/US05/33368 International Search Report and Written Opinion of the International Searching Authority mailed May 2, 2007.
(Continued)

*Primary Examiner* — Roy M Punnoose
(74) *Attorney, Agent, or Firm* — Procopio, Cory, Hargreaves & Savitch LLP; Noel C. Gillespie

(57) ABSTRACT

A particle detection system uses a reflective optic comprising a curved surface to detect high angle scattered light generated by a particle in a liquid medium, when a laser beam is incident on the particle. When the particles transit the laser beam, light is scattered in all directions and is described by MIE scattering theory for particles about the size of the wavelength of light and larger or Rayleigh Scattering when the particles are smaller than the wavelength of light. By using the reflective optic, the scattered light can be detected over angles that are greater than normally obtainable.

30 Claims, 18 Drawing Sheets

U.S. PATENT DOCUMENTS

| | | | |
|---|---|---|---|
| 3,989,381 | A | 11/1976 | Fulwyler |
| 4,167,335 | A | 9/1979 | Williams |
| 4,199,686 | A | 4/1980 | Brunsting et al. |
| 4,273,443 | A * | 6/1981 | Hogg .......................... 356/343 |
| 4,281,924 | A | 8/1981 | Auer et al. |
| 4,523,841 | A | 6/1985 | Brunsting et al. |
| 4,548,473 | A | 10/1985 | Lo et al. |
| 4,548,500 | A | 10/1985 | Wyatt et al. |
| 4,606,636 | A * | 8/1986 | Monin et al. ................ 356/338 |
| 4,710,025 | A | 12/1987 | Wyatt et al. |
| 4,716,123 | A | 12/1987 | Wood |
| 4,877,747 | A | 10/1989 | Stewart |
| 5,101,113 | A | 3/1992 | Hirleman, Jr. et al. |
| 5,125,737 | A | 6/1992 | Rodriguez et al. |
| 5,127,729 | A | 7/1992 | Oetliker et al. |
| 5,141,609 | A | 8/1992 | Sweedler et al. |
| 5,502,561 | A | 3/1996 | Hutchins et al. |
| 5,565,984 | A | 10/1996 | Girvin |
| 5,576,827 | A | 11/1996 | Strickland et al. |
| 5,614,726 | A * | 3/1997 | Kaye et al. .................. 250/574 |
| 5,633,503 | A | 5/1997 | Kosaka |
| 5,644,388 | A * | 7/1997 | Maekawa et al. ............. 356/73 |
| 5,650,847 | A | 7/1997 | Maltsev et al. |
| 5,663,503 | A | 9/1997 | Dam et al. |
| 5,721,433 | A | 2/1998 | Kosaka |
| 5,760,900 | A | 6/1998 | Ito et al. |
| 5,786,894 | A * | 7/1998 | Shields et al. ............... 356/338 |
| 5,962,853 | A | 10/1999 | Huth-Fehre et al. |
| 6,016,712 | A | 1/2000 | Warden et al. |
| 6,091,492 | A | 7/2000 | Strickland et al. |
| 6,177,994 | B1 | 1/2001 | Watson et al. |
| 6,252,658 | B1 | 6/2001 | Togawa et al. |
| 6,263,227 | B1 | 7/2001 | Boggett et al. |
| 6,347,374 | B1 | 2/2002 | Drake et al. |
| 6,407,812 | B1 | 6/2002 | Kurozumi et al. |
| 6,421,121 | B1 | 7/2002 | Haavig et al. |
| 6,469,786 | B2 | 10/2002 | Shimaoka |
| 6,515,737 | B2 | 2/2003 | Perry |
| 6,519,033 | B1 | 2/2003 | Quist et al. |
| 6,541,627 | B1 | 4/2003 | Ono et al. |
| 6,573,992 | B1 * | 6/2003 | Drake .......................... 356/338 |
| 6,590,652 | B2 * | 7/2003 | Quist et al. .................. 356/338 |
| 6,628,386 | B2 | 9/2003 | Davis et al. |
| 6,630,990 | B2 | 10/2003 | van't Oever et al. |
| 6,639,672 | B2 | 10/2003 | Haavig et al. |
| 6,713,019 | B2 | 3/2004 | Ozasa et al. |
| 6,760,107 | B1 * | 7/2004 | Drake .......................... 356/338 |
| 6,774,995 | B2 | 8/2004 | Quist et al. |
| 6,784,990 | B1 | 8/2004 | DeFreez et al. |
| 6,813,303 | B2 | 11/2004 | Matsuda et al. |
| 6,859,277 | B2 | 2/2005 | Wagner et al. |
| 6,934,022 | B1 | 8/2005 | Engelhardt |
| 6,972,424 | B1 | 12/2005 | Quist et al. |
| 7,057,724 | B1 | 6/2006 | Mead et al. |
| 7,072,038 | B2 | 7/2006 | Quist et al. |
| 2002/0071121 | A1 | 6/2002 | Ortyn et al. |
| 2002/0093641 | A1 | 7/2002 | Ortyn et al. |
| 2002/0141902 | A1 | 10/2002 | Ozasa et al. |
| 2002/0186372 | A1 | 12/2002 | Haavig et al. |
| 2003/0035105 | A1 | 2/2003 | Quist et al. |
| 2003/0086087 | A1 | 5/2003 | Quist et al. |
| 2003/0086608 | A1 * | 5/2003 | Frost et al. .................... 382/173 |
| 2003/0090657 | A1 | 5/2003 | Drake |
| 2003/0107734 | A1 | 6/2003 | Davis et al. |
| 2003/0227545 | A1 | 12/2003 | Soya et al. |
| 2004/0004716 | A1 | 1/2004 | Mavliev |
| 2004/0011975 | A1 | 1/2004 | Nicoli et al. |
| 2004/0201845 | A1 | 10/2004 | Quist et al. |
| 2005/0024641 | A1 | 2/2005 | DeFreez et al. |
| 2005/0151968 | A1 | 7/2005 | Drake et al. |
| 2005/0243322 | A1 * | 11/2005 | Lasker et al. ................. 356/432 |
| 2006/0261941 | A1 | 11/2006 | Drake et al. |
| 2007/0013910 | A1 * | 1/2007 | Jiang et al. ................... 356/336 |

FOREIGN PATENT DOCUMENTS

WO        9629571  A1     9/1996

OTHER PUBLICATIONS

PCT/US06/16950, International Search Report and Written Opinion of the International Searching Authority mailed Sep. 21, 2007.

PCT/US06/23043, International Search Report and Written Opinion of the International Searching Authority mailed Sep. 12, 2007.

PCT/US07/85975, International Search Report and Written Opinion of the International Searching Authority mailed Sep. 15, 2008.

PCT/US07/85976, International Search Report and Written Opinion of the International Searching Authority mailed Sep. 9, 2008.

PCT/US07/80609, International Search Report and Written Opinion of the International Searching Authority mailed Sep. 2, 2008.

Extended European Search Report and Opinion issued by the European Patent Office on Mar. 23, 2011 (11 pages).

Extended European Search Report and Opinion issued by the European Patent Office for EP 06784381.3 on Jun. 6, 2011 (7 pages).

* cited by examiner

SYSTEMS AND METHODS FOR A MULTIPLE ANGLE LIGHT SCATTERING (MALS) INSTRUMENT HAVING TWO-DIMENSIONAL DETECTOR ARRAY

CROSS-REFERENCE TO RELATED APPLICATIONS

This application claims priority as a Continuation under 35 U.S.C. 120 to U.S. patent application Ser. No. 11/453,278, entitled "Systems and Methods for a Multiple Angle Light Scattering (MALS) Instrument Having Two-Dimensional Detector Array," filed Jun. 13, 2006, which in turn claims priority to U.S. Provisional Application 60/690,535, filed Jun. 13, 2005, and also claims priority to and is a continuation-in-part of U.S. application Ser. No. 11/381,346, filed May 2, 2006, which claims priority to U.S. Provisional Application 60/676,730, filed May 2, 2005, and which also claims priority as a continuation-in-part application to U.S. patent application Ser. No. 11/231,350, filed Sep. 19, 2005. All of the above applications are incorporated herein in their entirety as if set forth in full.

BACKGROUND

1. Field of the Invention

The embodiments described herein relate to identifying particles, and in particular to identifying particles in a liquid using illumination incident at an angle and a two-dimensional camera for capturing scattered light from the particles.

2. Background of the Invention

A major concern for, e.g., water utilities is the detection and control of pathogenic microorganisms, both known and emerging, in potable water treatment and distribution. There are not only a number of chlorine resistant pathogens such as Cryptosporidium that can contaminate drinking water systems, but also potentially harmful microorganisms that can be introduced, either accidentally or intentionally, and propagate under suitable environmental conditions. Due to the length of time for standard laboratory methods to yield results, typically 24-72 hours, there has not been a reliable system to detect microbial contaminants in real-time and on line to provide a warning of pathogen contamination events. Because of these expanding challenges, there has been an accelerated development of rapid tests and real-time methods to address the pressing needs of the water treatment community.

Conventional microbiological methods can be used to detect some harmful microorganisms; however, such methods provide limited results. Analytical methods in microbiology were developed over 120 years ago and are very similar today. These methods incorporate the following steps: sampling, culturing and isolating the microbes in a suitable growth media by incubation, identifying the organisms through microscopic examination or stains, and quantifying the organisms. Cryptosporidium and Giardia form oocysts or cysts and cannot be cultured in conventional ways. To detect these protozoan pathogens, an amount of water containing suspected pathogens, typically 10 liters, is sent through a special filter to collect and concentrate the organisms. Then the filter is eluded and the organisms further processed, such as staining the organisms and sending the concentrated solution through flow cytometry, for example. These procedures, which can be found in Standard Methods or ASME, require ascetic technique in sampling and handling, skilled technicians to perform the analysis, and a number of reagents, materials, and instruments to obtain results. Practically, such methods have, therefore, proved to be time consuming, costly, and of little effectiveness for many current environmental field applications.

In order to reduce the amount of time to access microbiological results, a number of methods have been developed, mostly in the field of medicine. These faster tests have been improved and adapted to the environmental field and are generally categorized as 1) accelerated/automated tests 2) rapid tests and 3) contamination warning systems (CWS).

Accelerated tests are by grab sample and results can be obtained in 4 hours to 18 hours. Accelerated tests include immunoassays, ATP luminescence, and fluorescent antibody fixation. Rapid tests are also by grab sample and require manipulation of the sample to 'tag' the microbes with an identifiable marker or concentrate the microbe's genetic material (DNA) for subsequent identification. Results are normally available in 1-3 hours. These types of tests include Polymerase Chain Reaction (PCR) and Flow Cytometry.

Real-time contamination warning systems are continuous warning devices that detect contaminants and provide an 'event' warning within minutes to prompt further investigation or action. CWS include laser-based multi-angle light scattering (MALS) and multi-parameter chemical & particle instruments that detect water quality changes inferring potential biological contamination. Continuous, real-time detection of pathogens in water surveillance was first discovered in the late 1960's and has progressed through a series of development steps until the first public field demonstration in 2002.

MALS is an acronym for "multi-angle light scattering" and is based on laser technology, photo-detection, and computer signal processing. When coherent light strikes a particle, a characteristic scattering pattern is emitted. The scattering pattern encompasses many features of the particle, including the size, shape, internal structures (morphology), particle surface, and material composition (organic or inorganic). Each type of microorganism will scatter light giving off a unique pattern called a 'bio-optical signature'. Photo-detectors collect the scattered light and capture the patterns which are then sent to an on-board computer. A microorganism's bio-optical signature is then compared against known pattern classifications in the detection library for results.

Presently, a detection system capable of meeting all of the 'ideal detection system' parameters, e.g., as cited by the American Water Works Association does not exist. Conventional MALS devices and methods often differ in the amount of time to obtain results, degree of specificity, sampling frequency, concentration sensitivity, operating complexity, and cost of ownership. The events of Sep. 11, 2001, represented an escalation in the means and effects of terrorist attacks and raised awareness of the vulnerability of major infrastructures such as transportation, finance, power and energy, communications, food, and water. A re-examination of the security of critical assets was initiated, and some action has been taken in the United States to protect our drinking water. When a water treatment system is compromised, action needs to be taken to bring it into compliance in as timely a manner as possible. If an online MALS system is used in conjunction with other standard tests for bacteria and protozoa parasites, then the time to react is reduced and the resulting number of people who could potentially get sick is reduced. In some cases, proper action can be taken even before there is any significant health risk.

SUMMARY

A particle detection system uses a reflective optic comprising a curved surface to detect high angle scattered light generated by a particle in a liquid medium, when a laser beam is incident on the particle. When the particles transit the laser beam, light is scattered in all directions and is described by MIE scattering theory for particles about the size of the wavelength of light and larger or Rayleigh Scattering when the particles are smaller than the wavelength of light. By using the reflective optic, the scattered light can be detected over angles that are greater than normally obtainable. For example, the scattered light can be measured through an angle 90°.

These and other features, aspects, and embodiments of the invention are described below in the section entitled "Detailed Description."

BRIEF DESCRIPTION OF THE DRAWINGS

Features, aspects, and embodiments of the inventions are described in conjunction with the attached drawings, in which.

DETAILED DESCRIPTION OF THE PREFERRED EMBODIMENTS

Figure 1:
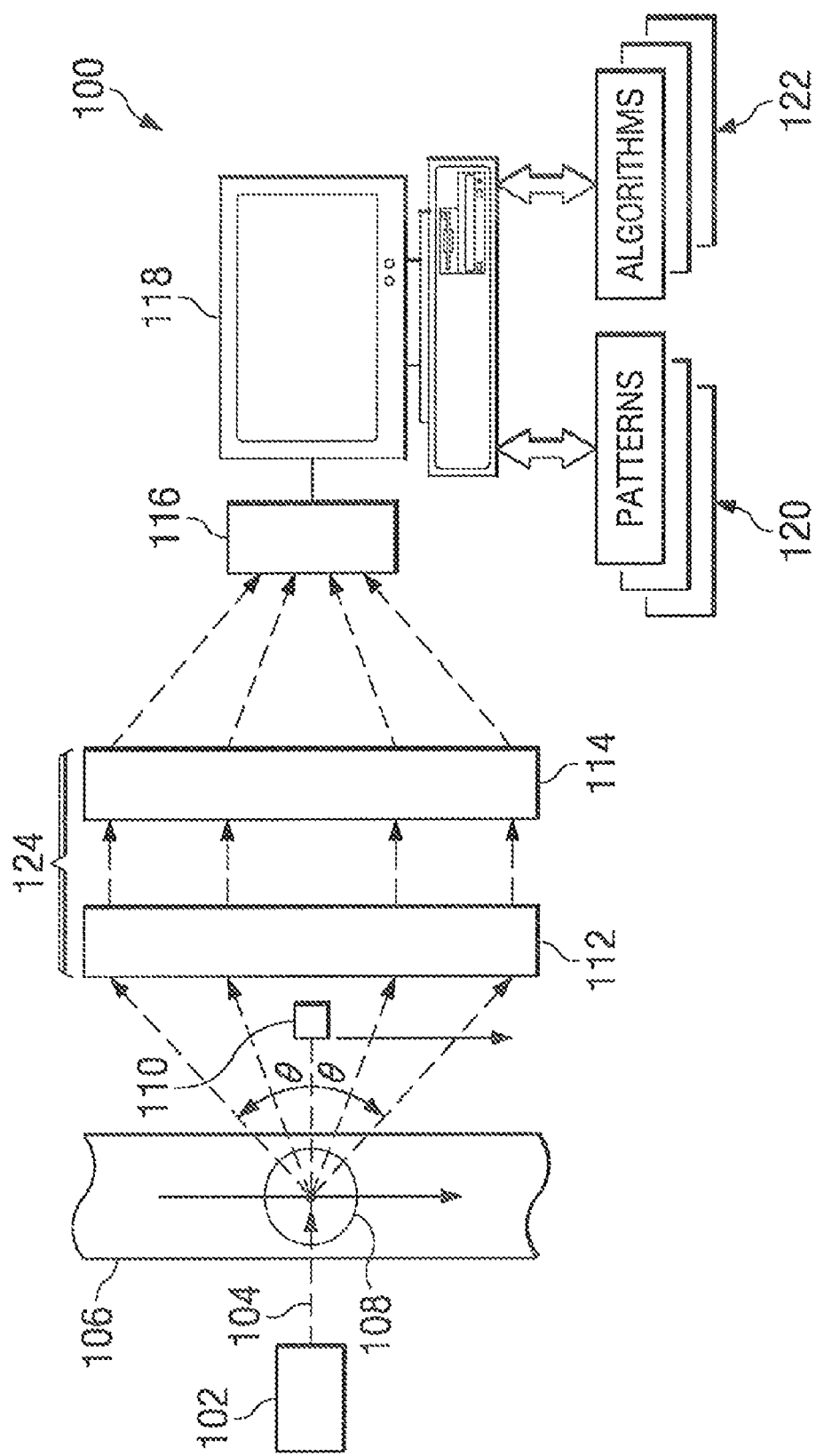
FIG. 1 is a diagram illustrating an example embodiment of a particle detection system.

In the following description, all numbers disclosed herein are approximate values, regardless whether the word "about" or "approximately" is used in connection therewith. They may vary by up to 1%, 2%, 5%, or sometimes 10 to 20%. Whenever a numerical range with a lower limit, $R_L$, and an upper limit $R_u$, is disclosed, any number R falling within the range is specifically and expressly disclosed. In particular, the following numbers R within the range are specifically disclosed: $R=R_L+k*(R_u-R_L)$, wherein k is a variable ranging from 1% to 100% with a 1% increment, i.e. k is 1%, 2%, 3%, 4%, 5%, ..., 50%, 51%, 52%, ..., 95%, 96%, 97%, 98%, 99%, or 100%. Moreover, any numerical range defined by two numbers, R, as defined in the above is also specifically disclosed. It is also emphasized that in accordance with standard practice, various features may not be drawn to scale. In fact, the dimensions of the various features may be arbitrarily increased or reduced for clarity of discussion.

Embodiments of the present invention provide a method for real-time particle detection that uses advancements in computing power, special optics, photonics engineering, advanced signal processing, and complex algorithms, in order to provide a MALS detection system that provides simplicity, cost effectiveness, speed, and reliability. The systems described in the embodiments below are analytical system using MALS where a side stream from a water source flows through a transparent flow cell. A laser directs a beam of light into the flow cell and through the water stream. In certain embodiments, the water is first characterized for background interferences to distinguish foreign particles from the pathogens' signatures resulting in a custom detection library in each particular installation.

In operation, particles pass through the beam, the scattered light is emitted and captured by the detectors, converted to a digital signal, and finally sent to the computer's microbial library for analysis. When a pattern is recognized by the library, the organisms are classified within minutes. The data can be transmitted to a user screen and remote communications equipment. In certain embodiments, upon reaching a pre-set threshold level, an 'alert' can be generated and an instantaneous sample can be automatically extracted for further identification and confirmation.

Water, or other liquids for that matter, can be monitored continuously as it passes through the flow cell at a defined rate. This provides a much higher probability of detecting and classifying microorganisms compared to intermittent grab samples. The speed and performance can be further enhanced when the 1) microbial concentration level is high, 2) the water, or liquid, is of high 'clarity' or purity, 3) microorganisms match defined bio-optical signatures in the library versus an 'unknown', and 4) the particles are of larger size, e.g., >1 micron, giving distinct scattering patterns.

In certain embodiments, if an unclassified organism is detected, the system can categorize it as an 'unknown' and still provide an 'alert' if a certain threshold level is reached.

Thus, the systems and methods described below can provide valuable early warnings of potential microbial contamination. The system described can be implemented economically and with extremely low operating costs. Further, the systems described do not use reagents or require costly consumables and can be compact, rugged, and easy to use, while requiring minimal operator training or expertise. In certain embodiments, 'warning' and 'alert' levels can be adjusted according to the requirements of a particular implementation and can interface with a number of communication protocols to provide immediate information for quality control or security personnel.

FIG. 1 is a diagram illustrating an example particle detection system configured in accordance with one embodiment of the systems and methods described herein. Many of the embodiments described below are used for detecting microorganism such as Cryptosporidium and Giardia; however, it will be understood that the systems and methods described herein can be used to detect any particle capable of detection using the systems and methods described, such as bacteria and yeasts. Bacteria are typically smaller than Cryptosporidium and Giardia ranging from 500 nanometers diameter upwards to 2 microns and from oval to rod shape. Yeasts are typically the size of Giardia or larger. Further, while the embodiments described below generally describe detected particles in water, it will be understood that the systems and methods described can be used to detect particles and other liquids, and even in other media such as air.

System 100 comprises a light source 102 configured to provide illumination 104 to a target area 108. In the embodiment of FIG. 1, target area 108 is within a flow cell 106. Water intended to be interrogated for various particles or microorganisms can flow through flow cell 106, e.g., in a downward direction as indicated. Illumination 104 will encounter particles in target zone 108, which will cause the illumination to scatter in a manner different than the illumination transmitted through the surrounding fluid medium.

System 100 can also comprise an optical system 124. Optical system 124 can comprise several elements. For example optical system 124 can comprise a lens, or lens system 112 as well as an optical element 114. The system 100 can also comprise a detector, detector system, or detector array 116, which can be interfaced with a processing system 118.

Light source 102 can be configured to deliver a structured light pattern, or illumination. Thus, light source 102 can be, e.g., a coherent light source, such as a laser. Depending on the embodiment, light source 102 can comprise a single light source, such as a single laser, or a plurality of light sources, such as a plurality of lasers. Further, the wavelength of the light source can be at a fixed wavelength. Alternatively, when multiple light sources are used, the light sources can have several discrete wavelengths.

Accordingly, light source 102 can be a laser configured to produce a laser beam 104. When laser beam 104 strikes a particle within target area 108, the particle will cause the beam to scatter in a pattern that is different than the pattern produced due to beam 104 traveling through the water flowing in flow cell 106. Optical system 124 can be configured to then pick up the scattered light and direct it onto detector 116.

Detector 116 can actually be a plurality of detectors, such as a plurality of detectors arrayed in different positions around target area 108. Alternatively, detector 116 can comprise an array of photo detectors. For example, in one embodiment, detector 116 can actually comprise a linear array of photo detectors configured to detect the scattered light and generate an electrical signal having an amplitude corresponding to the amplitude of the detected light. In one implementation, for example, a Charge Coupled Device (CCD) can be used for detector 116. CCDs are readily available with thousands of pixels, wherein each pixel can form an individual photo detector. In another implementation for example, a 2 dimensional array of photodiodes or avalanche photodiodes of 64, 128, 256, or 512 total pixels can be used to increase the total dynamic range of the detector as compared to a CCD.

Detector 116 can be configured to generate an electrical signal, or signals, reflective of the light pattern incident on detector 116. The signals can then be provided to processing system 118 for further analysis. As described above, processing system 118 can convert the signals into a pattern using various algorithms 122. Processing system 118 can also comprise the memory configured to store a plurality of optical signatures, or patterns 120 that are associated with various particles, or microorganisms of interest.

Thus, processing system 118 can compare the pattern generated using algorithms 122 to one of the stored patterns 120 in order to identify particles within target zone 108.

As mentioned above, algorithms 122 and patterns 120 can be used to determine many features of particles being identified within target zone 108, e.g., including the size, shape, internal structures or morphology, particle surface, and material composition, i.e., organic or inorganic. For example, certain embodiments can use Multiple Analysis Of Variance (MANOVA) algorithms, neuro-networks, simulated and annealing, algorithm independent machine learning, physiologic, grammatical methods, and other algorithmic techniques for pattern generation and recognition. It will understood, however, that the systems and methods described herein are not limited to any specific algorithms or techniques, and that any algorithm or technique, or a combination thereof, that could be used to perform the processes described herein can be used as required by a particular implementation.

Particles within target zone 108 will cause light from laser beam 104 to scatter as illustrated in FIG. 1. Light scattering from target zone 108 at an angle greater than 8 from the optical axis of beam 104 will be internally reflected within flow cell 106 at the interface of flow cell 106 with the external atmosphere. Thus, only light at angles less than 8 can escape and be picked up by optical system 124.

In certain embodiments, a spherical lens (not shown) completely surrounding the flow cell, except for the flow cell inlet and outlet, can be placed at the interface of flow cell 106 in order to allow light scattered at any angle to the lens to pass through the lens to optical system 124. Of course, including such a spherical lens increases the complexity and cost of system 100.

Light passing through target zone 108 along the optical axis of beam 104 will generally be of a much greater intensity than that of the scattered light beams. The intensity of the beam along the optical axis can be so great that it can essentially prevent, or degrade detection of the scattered light beams. Accordingly, a beam stop 110 can be included in order to deflect beam 104 and prevent it from entering optical system 124 and being detected by detector 116.

The light scattered by a particle within target zone 108 can enter optical system 124, which can comprise an optical element 114. Optical element 114 can be configured to direct the scattered light onto detector 116. Specifically, optical element 114 can be configured in such a way that it can direct light traveling along a given path to an appropriate position on detector 116 or to an appropriate detector within an array of detectors comprising detector 116. For example, in one embodiment, optical element 114 can be a holographic optical element constructed so that each refracting section refracts, or redirects light from one of the scattered paths so that it falls on the correct location of detector 116. In other embodiments, optical element 114 can comprise a zone plate lens that can be configured to map the distance from the central optical access to a unique mapping that is useful for high speed scanning.

In certain embodiments, the scattered light may need to be collimated after it passes through target zone 108. Thus, a converging lens 112 can be included in optical system 124. A converging lens can be configured to reduce the angle spread for the various scattered light rays. In other words, a converging lens can be configured to collimate or converge the spread light rays. In other embodiments, some other optical device can be used to collimate the scattered light rays. It will also be apparent, that certain embodiments may not need an optical lens 112, i.e., collimation may not be necessary depending on the embodiment. Thus, optical system 124 mayor may not contain an optical lens 112, or a collimator, as required by the specific implementation.

As mentioned above, detector 116 can actually comprise a plurality of detectors such as a linear detector array or 2 dimensional array such as a Charge Coupled Device (CCD) or for better dynamic range, a 2 dimensional array of photodiodes or avalanche photodiodes. In one embodiment, for example, detector 116 can actually comprise a linear photo diode camera, e.g., a 128-pixel linear photo diode camera. In another embodiment, a square array of photodiodes may be used for detector 116. In yet another embodiment, an array of photodiodes arranged in segmented concentric circles may be employed for detector 116.

Figure 1A:
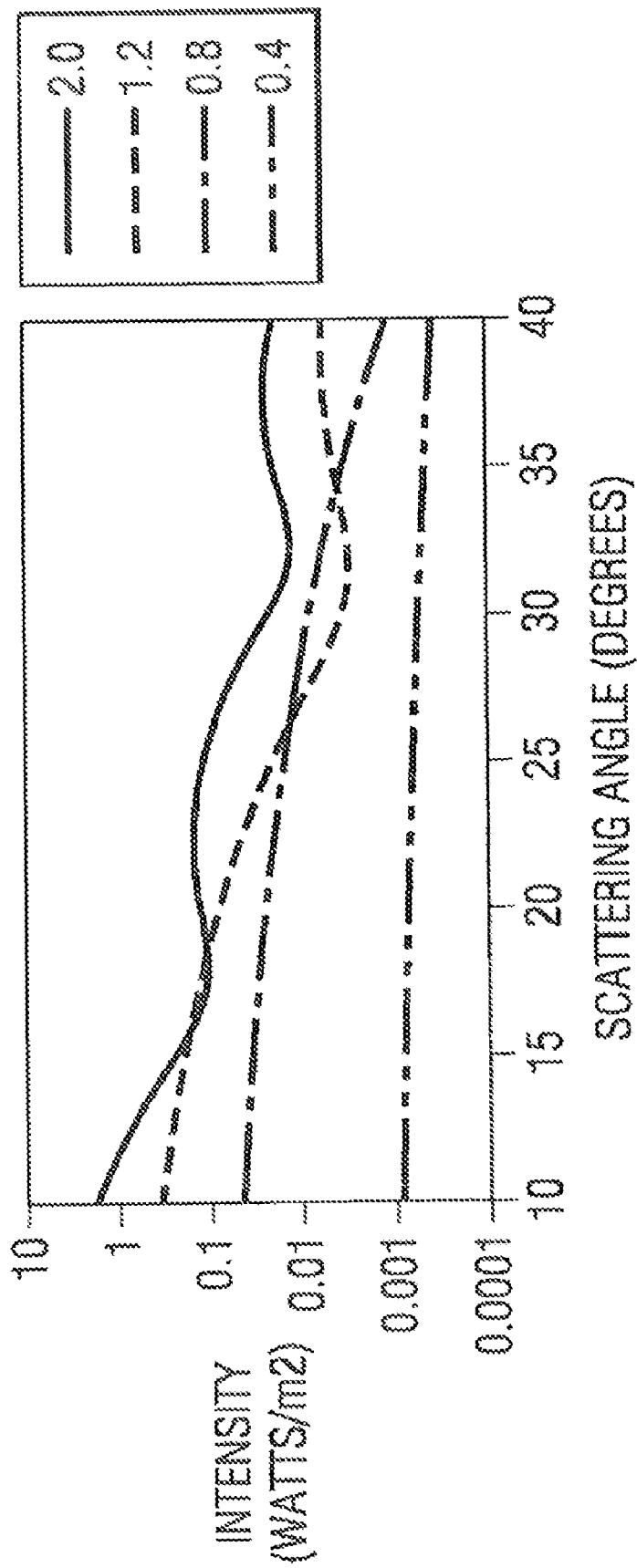
FIG. 1A is a plot showing the orders of magnitude in detector dynamic range required for bacterias.

Certain embodiments take advantage of the low-cost and extremely high computing horsepower provided by the latest PC chips, operating systems, and software, along with a unique photodiode 2-dimensional array camera system. These embodiments can be optimized for the detection and classification of microorganisms vs. other particles in water (typically silica), a process that is still difficult nonetheless. Microorganisms can range in size from 400 nanometers to 12 microns. By using the MIE calculations from Philip Laven's program (found at www.philiplaven.com). a pioneer in this field, to generate scattered intensities, FIG. 1A provides a plot that shows that over 3 orders of magnitude in detector dynamic range is required for bacterias (400 nm to 2 micron range).

Figure 1B:
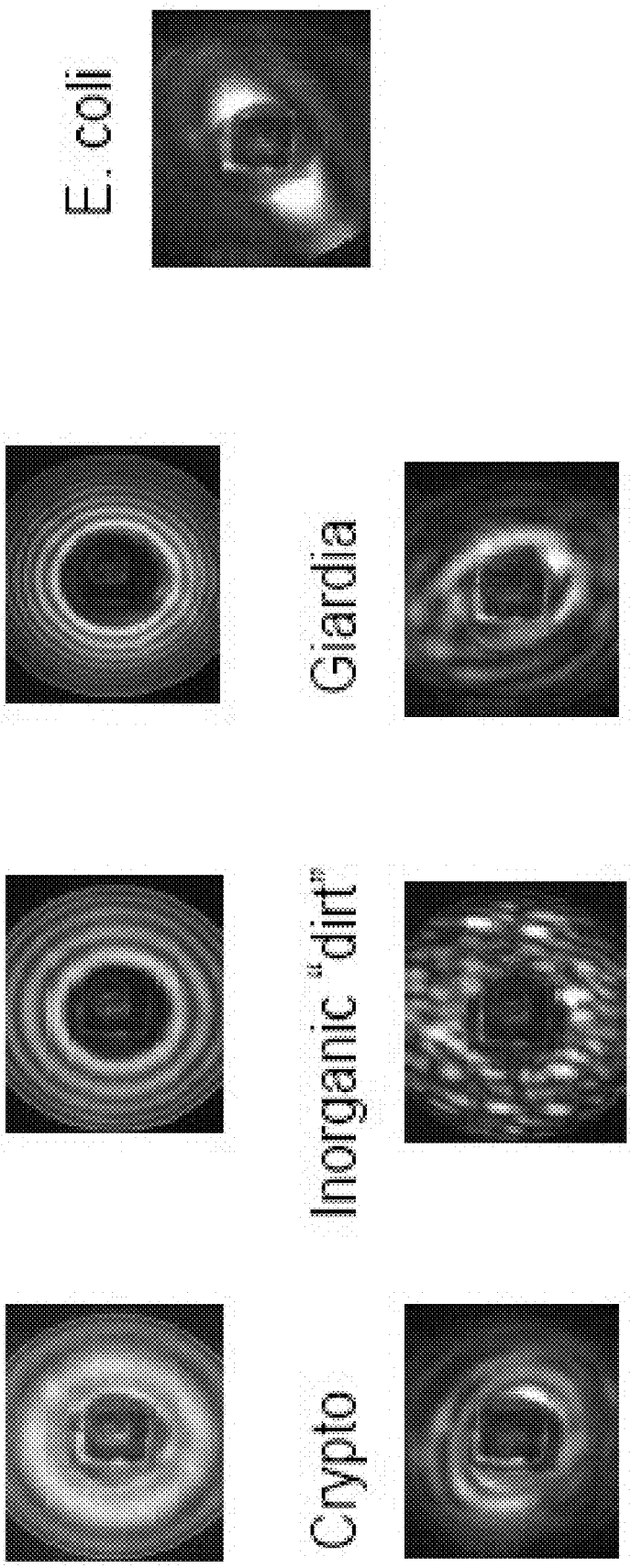
FIG. 1B illustrates 2-D scatter patterns from various particles taken with a MALS system employing a 2-D camera as disclosed herein.
Figures 1, 1C:
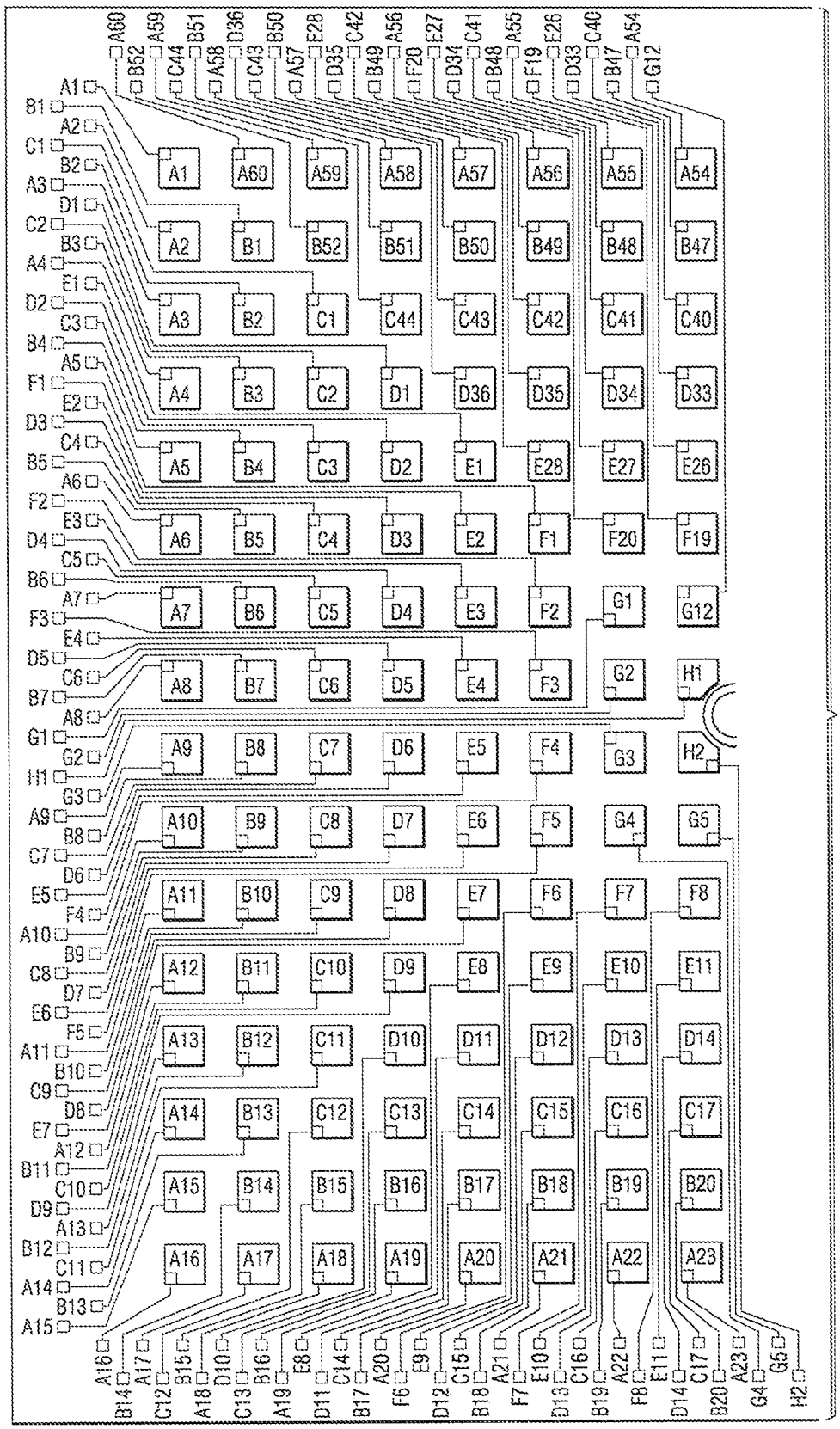
FIG. 1C illustrates an exemplary layout of a preferred embodiment of the 2-dimensional photodiode array.

An exemplary embodiment of a 2-D camera that can be used in conjunction with the systems and methods described herein can be configured to use a very high-speed (frame rate) 2 dimensional photo-diode array to provide high dynamic range, and limited pixel resolution to provide fast computer algorithms and high sensitivity. FIG. 1B illustrates 2-D scatter patterns from various particles taken with a MALS system employing a 2-D camera as disclosed herein. FIG. 1C illustrates an exemplary layout of a preferred embodiment of the 2-dimensional photodiode array. In this embodiment, there are 256 active elements arranged in a 16×16 square grid. Each pixel is approximately 1.1 mm square and they are laid out on 1.5 mm center to center spacing.

Regardless of the type of detector 116 employed, optical element 114 will be selected so as to complement detector 116 by directing the scattered light rays onto the appropriate pixel, or a section of detector 116; however, in certain embodiments, optical element 114 may not be needed. For example, in certain embodiments, the scattered light rays are incident directly onto detector 116.

Figures 1, 1C, 2:
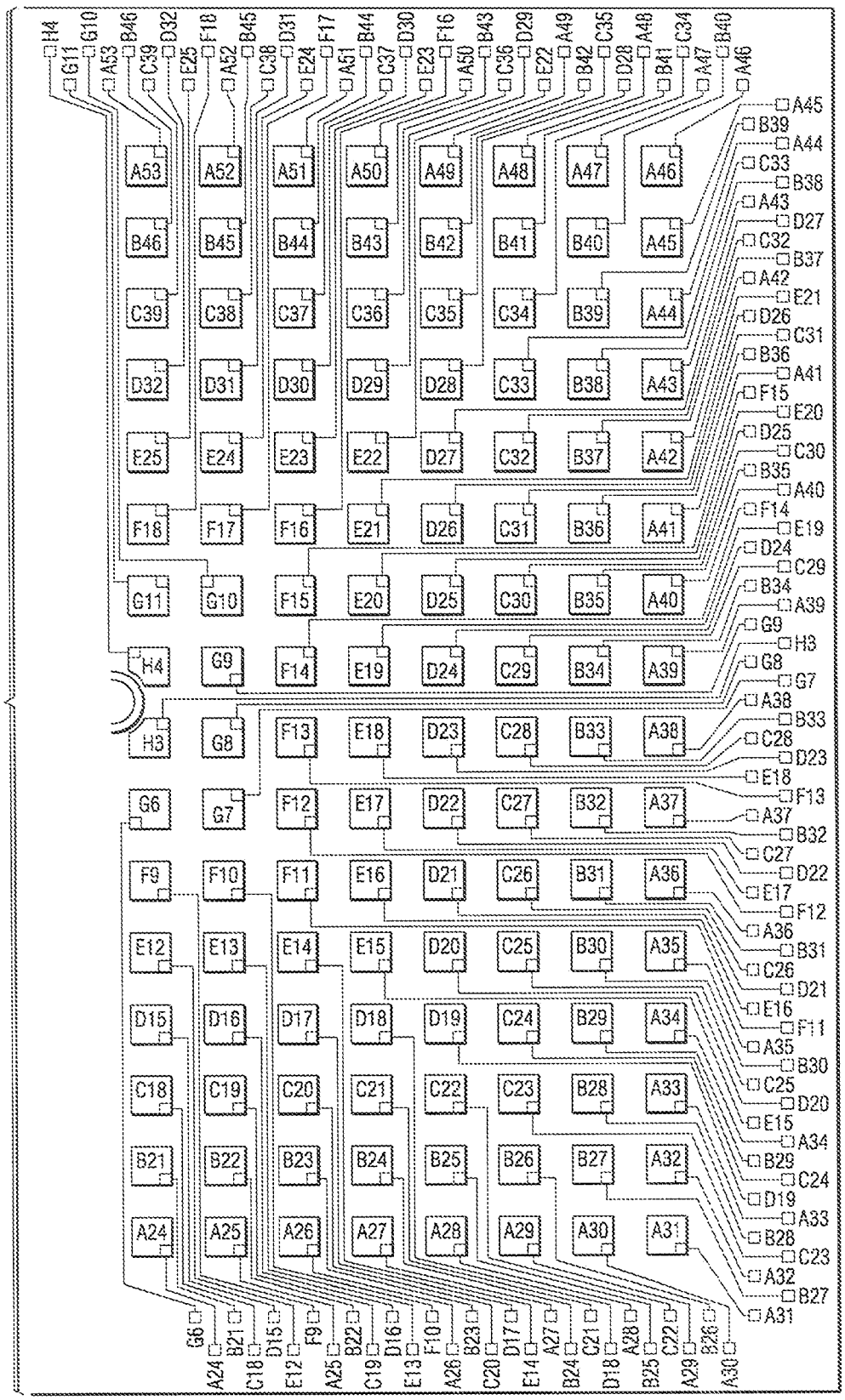
FIG. 2 is a diagram illustrating another example embodiment of a particle detection system.
Figure 2:
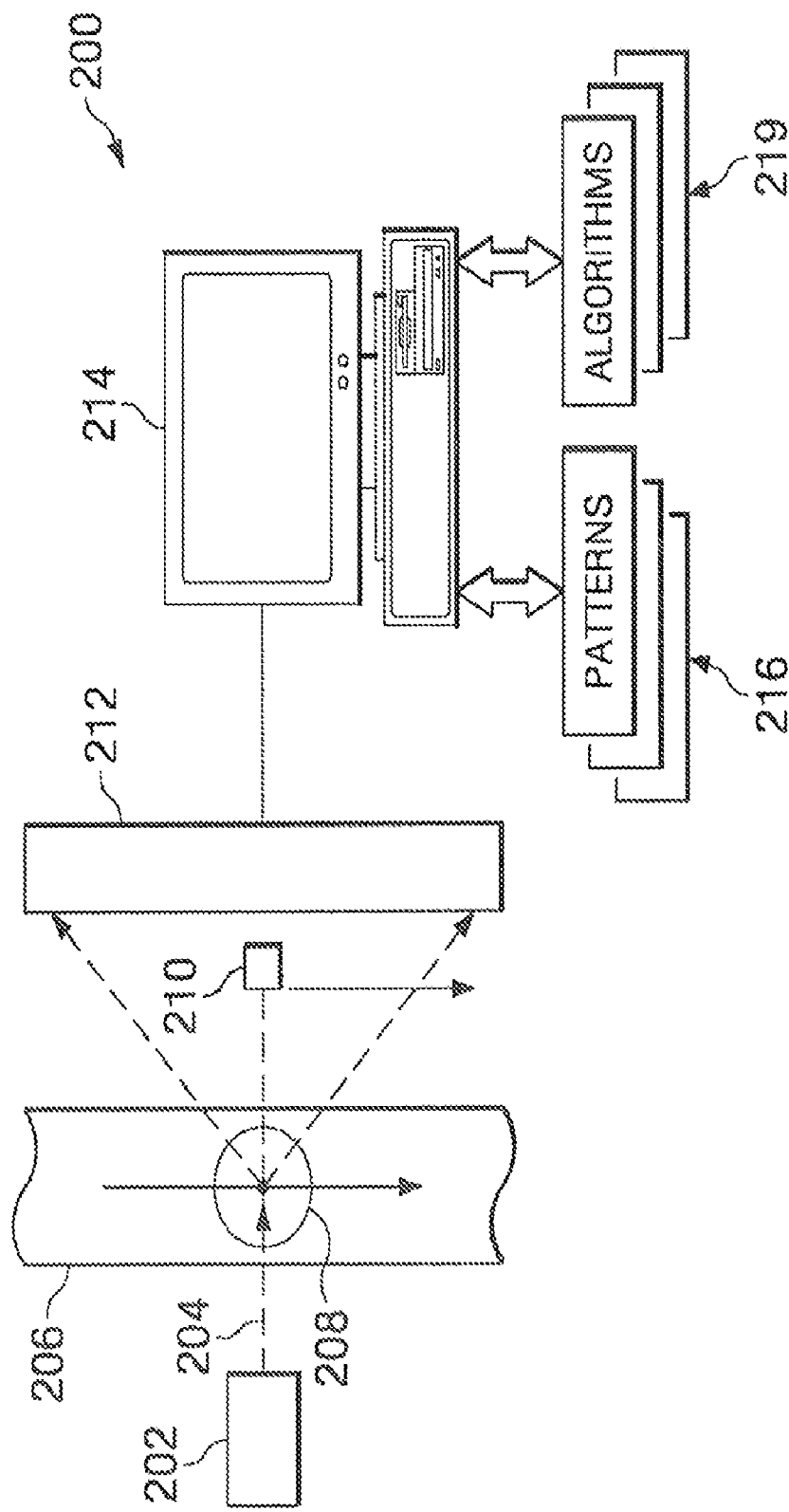

FIG. 2 is a diagram of a particle detection system 200 that does not include an optical element. Thus, system 200 comprises a light source 202, such as a laser, that produces a beam 204 that is incident on particles in target zone 208 within a fluid flowing in flow cell 206. The particles scatter beam 204 and the scattered beams are then incident directly on a detector 212. Detector 212 then produces electrical signals based on the incident scattered light rays and provides the electrical signals to processing system 214. Processing system 214 can, like processing system 118, be configured to generate a pattern from the electrical signals using algorithms 218 and compare them against stored patterns 216 in order to identify particles within target zone 208.

In the embodiment of FIG. 2, a beam stop 210 is still required to reflect the light ray traveling along the optical axis.

For example, in one embodiment, detector 212 can comprise a 64-pixel detector array, while in other embodiments, detector 212 can comprise a 128-pixel detector array. In certain embodiments, it can be preferred that detector 212 comprise a 256-pixel detector. Arrays larger than 256-pixels can be utilized in the present invention at a penalty of increasing cost and complexity. It should also be noted, that detector 212 can comprise conditioning amplifiers, multiplex switches, an Analog-to-Digital Converter (ADC) configured to convert analog signals produced by the detector pixel elements into digital signals that can be passed to processing system 214. An example embodiment of a detector is described in more detail below with respect FIG. 14.

Further, system 200 can include telescoping optics (not shown) in order to collimate the scattered light rays if necessary.

As mentioned above, each type of particle, or microorganism, will scatter light giving off a unique pattern called an optical signature, or bio-optical signature. A detector, such as detector 212, can collect the scattered light and capture the patterns. Electrical signals representative of the pattern can then be provided to a processing system such as processing system 214. FIGS. 3 and 4 illustrate example optical signatures for two different types of particles.

Figure 3A:
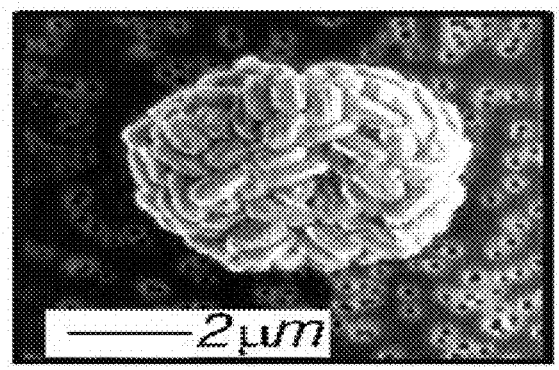
FIG. 3A is a picture of B. suptilis spores.
Figure 3B:
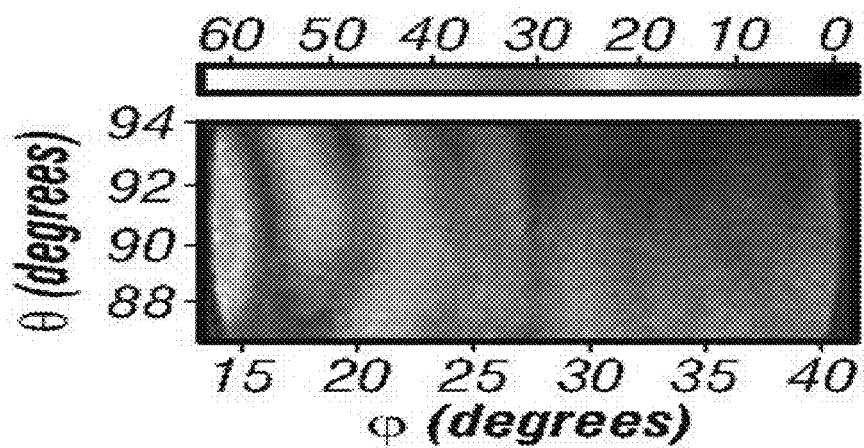
FIGS. 3B and 3C are pictures illustrating example optical signatures that can be generated by the systems of FIGS. 1 and 2 for the B. suptilis spores of FIG. 3A.
Figure 3C:
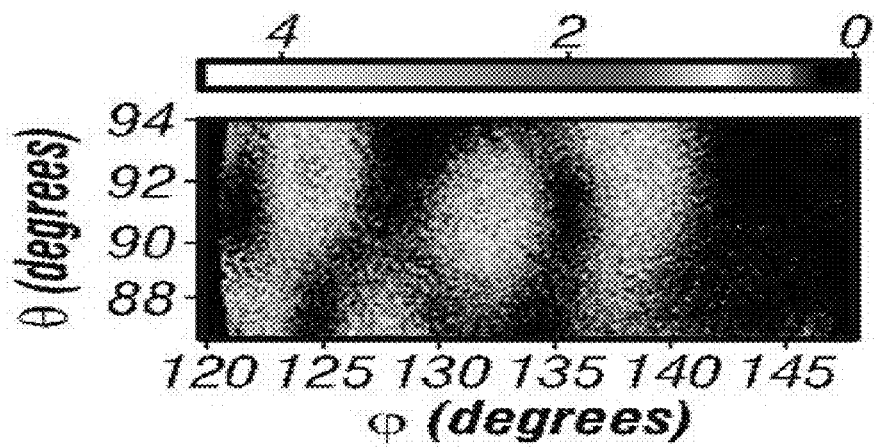
Figure 4A:
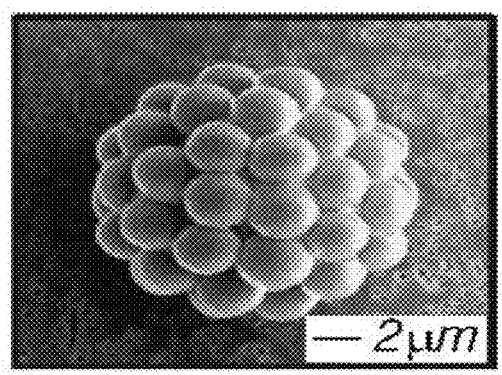
FIG. 4A is a picture of a ball of plastic spheres.
Figure 4B:
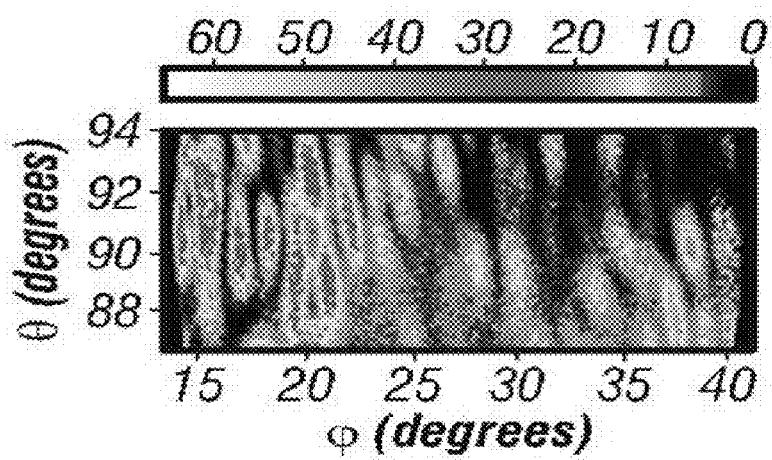
FIGS. 4B and 4C are pictures illustrating example optical signatures that can be generated by the systems of FIGS. 1 and 2 for the ball of plastic spheres of FIG. 4A.
Figure 4C:
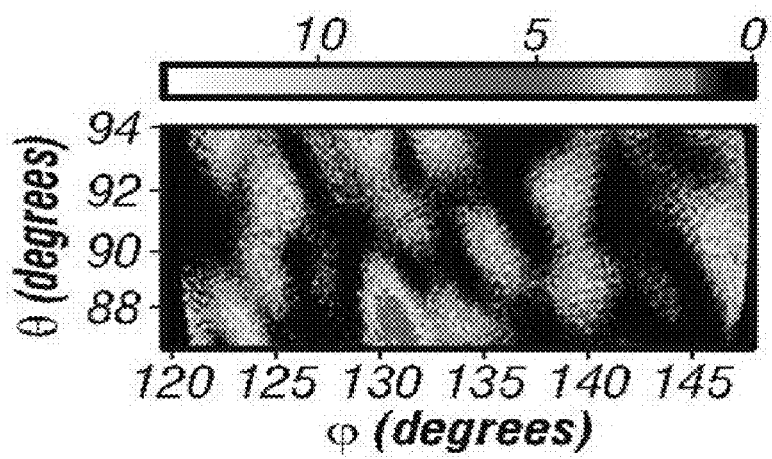

FIG. 3A is a picture illustrating subtilis spores, a microorganism. FIGS. 3B and 3C are pictures illustrating the optical signature associated with the subtilis spores of FIG. 3A. FIG. 4A is a picture illustrating a ball of plastic spheres. FIGS. 4B and 4C are diagrams illustrating the optical signature for the ball of plastic spheres in FIG. 4A. Thus, the optical signatures, or patterns, of FIGS. 3A-3C and 4A-4C, which can be produced using, e.g., algorithms 218, can be compared to patterns stored within the processing system.

Figure 5:
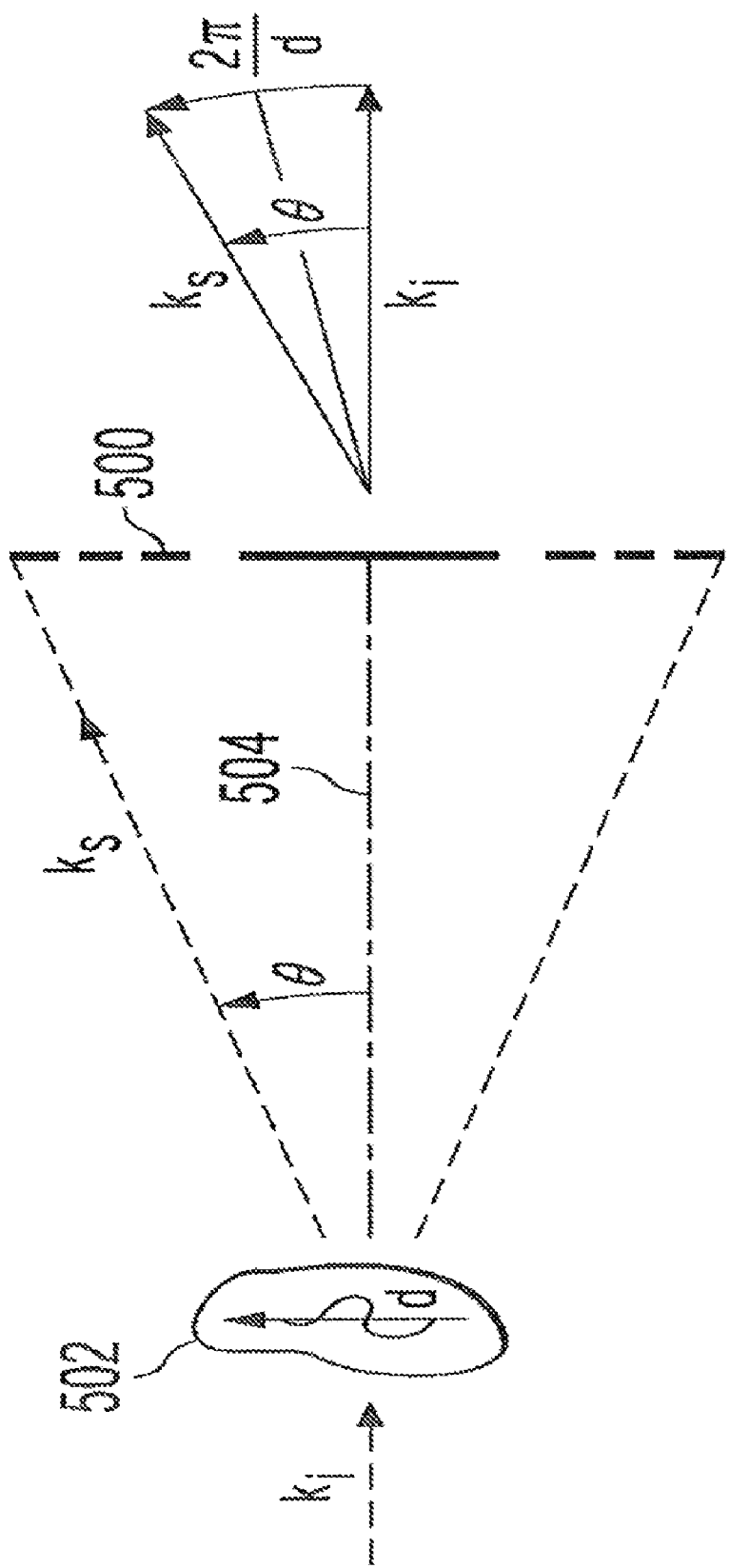
FIGS. 5-7 are diagrams illustrating a technique for using illumination incident at an angle in a light scattering detection system, such as the systems of FIGS. 1 and 2.

As noted above, if some form of spherical lens, or other device, is not used, then only scattered light rays with an angle less the e would be detected; however, if the illumination beam is incident at an angle, then light can be measured through twice the original measured scattering angles and still be captured by the detector. The scattering angle of the scattered radiation is inversely proportional to the size of the feature or object from which it was scattered, thus smaller features scatter light into larger angles. Illuminating the sample at angle permits radiation scattered from smaller features to still be captured by the detector's optical system; thus, a greater resolution can be achieved. This is illustrated by FIGS. 5-7.

When illumination is incident upon a particle 502 along an optical axis 504, vector $k_i$ can be used to represent the illumination. As illumination incident along vector $k_i$ encounters particle 502, it will be scattered through a sphere of 360 degrees but only detected through a range of angles up to Θ. Thus, a scattered light ray at the outer edge of the detector range can be represented by vector $k_s$.

Figure 6:
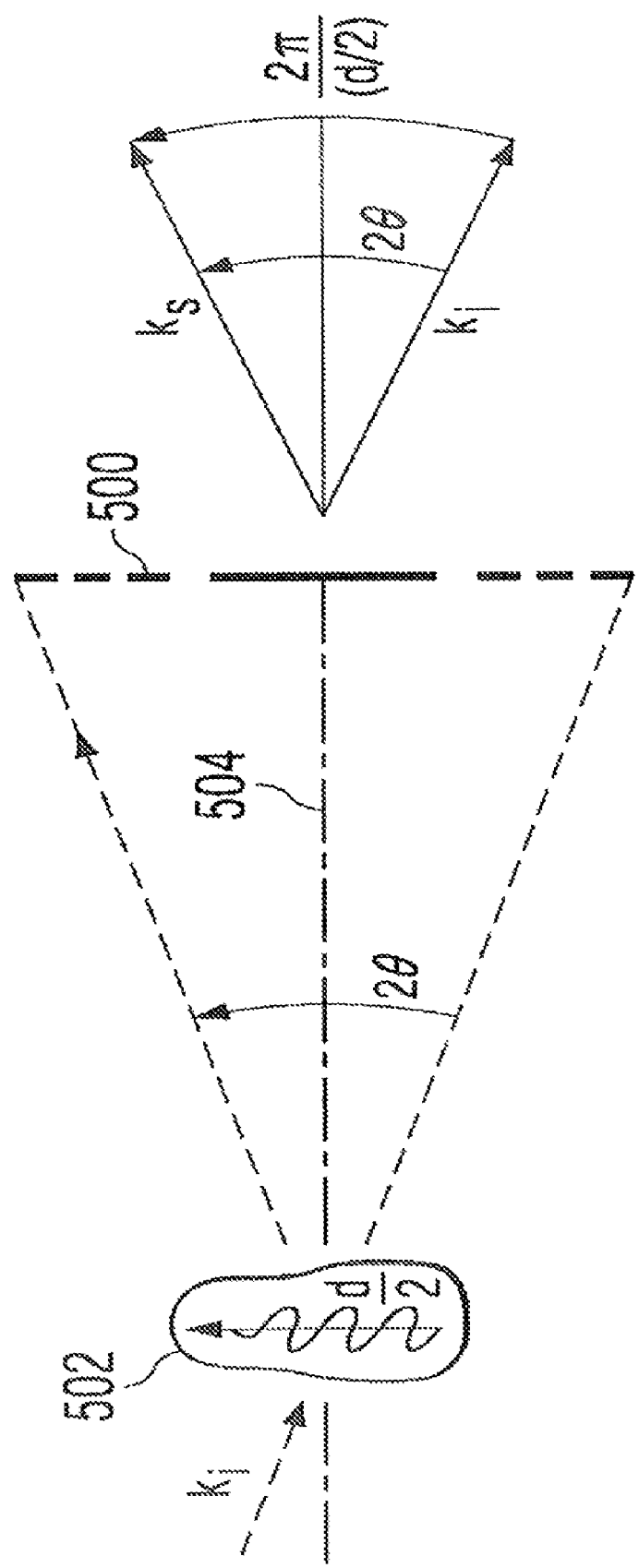

If, however, the illumination is incident at an angle illustrated by vector $k_i$ in FIG. 6, then the detector will be able to see light scattered through a greater range of angles. For example, the scattered light rays will be measured through an angle of 2Θ. As a result, objective 500 can collect scattered light rays scattered through twice the angle as compared to the system in FIG. 5. Thus, the resolution of the system illustrated in FIG. 6 would be twice that of the system illustrated in FIG. 5.

Figure 7:
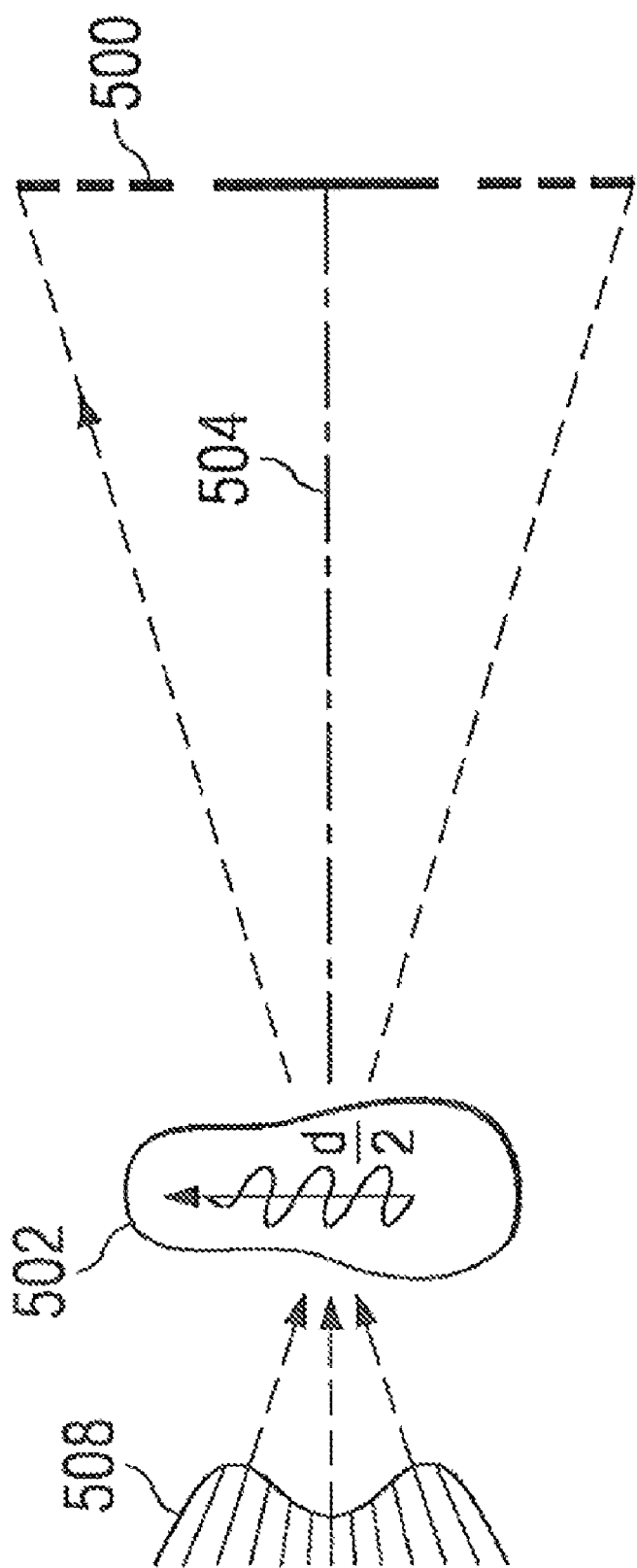

FIG. 7 is a diagram illustrating that the same effect can be achieved using a plurality of incident beams 508 that include beams incident at an angle from above and below the optical axis 504. Switching on or off the individual laser beams can provide additional multiple angles without having to provide additional detectors. If the switching is fast enough compared to the transit of the particle through the beam, then the additional angles can be obtained for the same particle.

It should be noted that objective 500 in FIGS. 5-7 can be a zone plate as well as another conventional optical element, including a holographic optical element.

Figure 8:
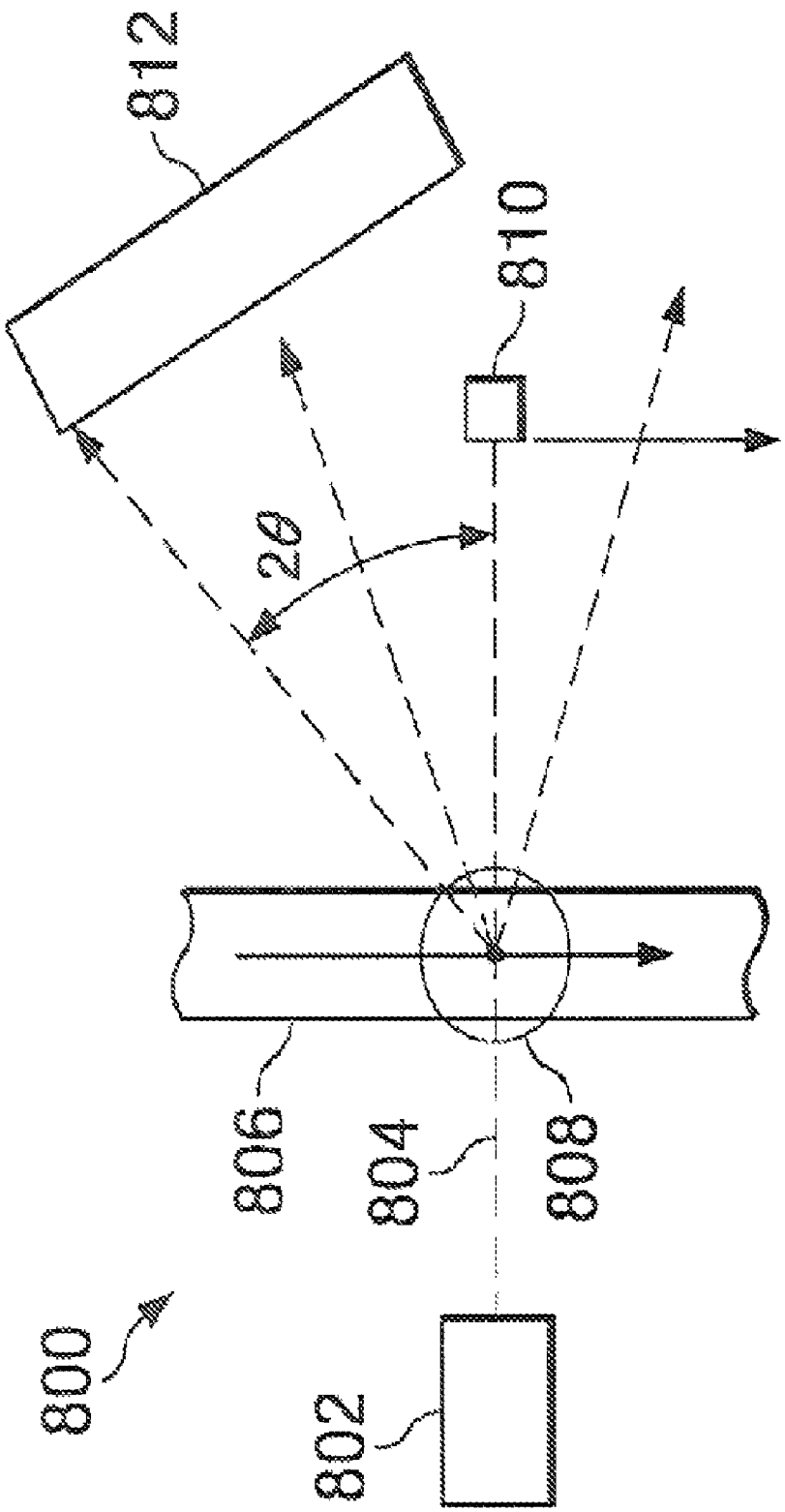
FIG. 8 is a diagram illustrating an example particle detection system that implements the technique of FIGS. 5-7 in accordance with one embodiment.
Figure 9:
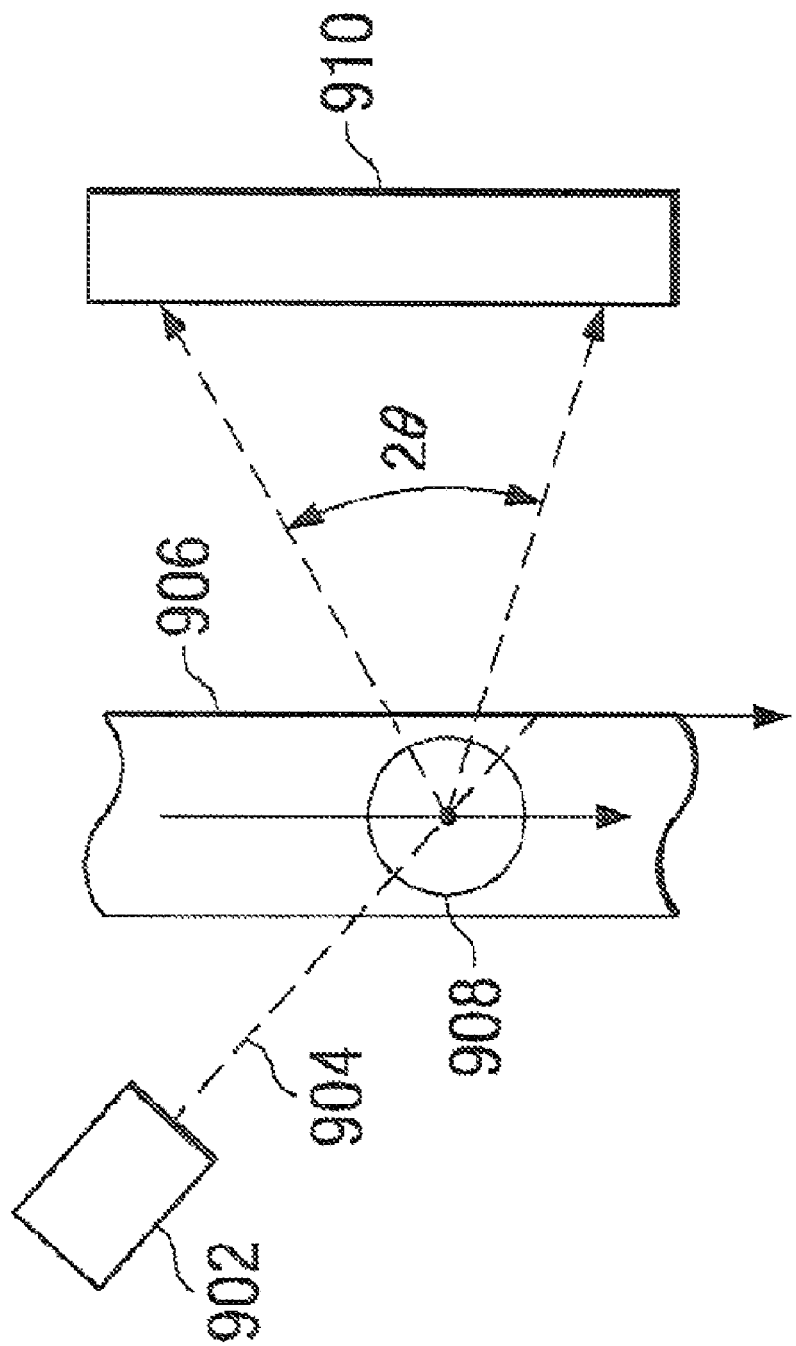
FIG. 9 is a diagram illustrating an example particle detection system that implements the technique of FIGS. 5-7 in accordance with another embodiment.

FIGS. 8 and 9 illustrate that the technique depicted in FIGS. 6 and 7 could be achieved by altering the position of the optical detector or by configuring the light source so that the illumination is incident at an angle upon the target zone. Thus, FIG. 8 is a diagram illustrating an example particle detection system 800 in which an optical detector 812 has been repositioned so as to capture scattered light rays scattered to an angle 2Θ. In FIG. 8, a light source 802, such as a laser, produces a beam 804 that is incident on particles within target zone 808. It should be noted that a beam stop 810 can still be required within system 800 to deflect the beam traveling along the optical axis.

It will be understood that system 800 can comprise a processing system, but that such system is not illustrated for simplicity.

FIG. 9 is a diagram illustrating an example particle detection system 900 in which optical source 902 is configured such that beam 904 is incident upon target zone 908 at an angle equal to or greater than the critical angle defined by the phenomenon of total internal reflection. In the system of FIG. 9, by selecting the incident angle such that the beam experiences total internal reflection, the beam 904 is internally reflected within flow cell 906, and thus a beam stop is not required. This can lower the cost and complexity of system 900 and can, therefore, be preferable.

Again, it will be understood that system 900 can comprise a processing system, but that such system is not illustrated for simplicity.

As mentioned above with respect to FIG. 1, angles larger than Θ will be reflected internally within flow cell 106. In general, collecting high angle scattered light from an object in a liquid medium requires some mechanism to prevent the internal reflection of the high angles being sought. This problem can be referred to as Total Internal Reflection (TIR) of the high-angle scattered light. TIR can occur at high to low indexes of refraction interfaces within the optics of the instrument or system being used to observe or collect the scattered light, e.g., the interface between flow cell 106 and the external atmosphere.

In certain embodiments, a second surface curved mirror reflecting optic can be used to collect and reflect the light. Such an optic can allow easy capture of light angles up to 90° for all azimuthal angles, when the sample is index coupled with the non-reflecting surface of the collection optic. Such an optic can prevent TIR issues at angles greater than approximately 40°.

Figure 10:
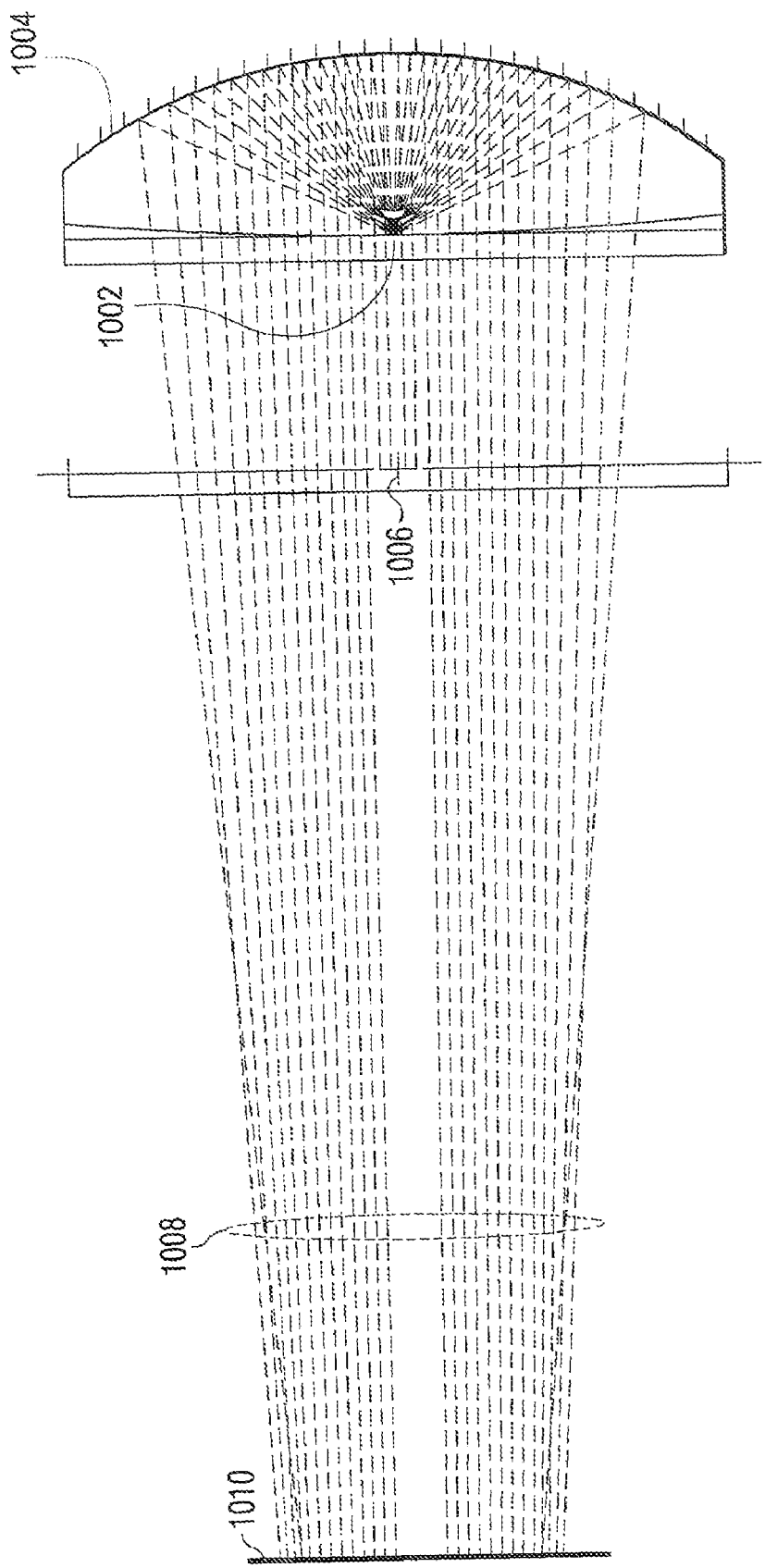
FIG. 10 is a diagram illustrating a spectrometer ray trace for light scattered by a particle suspended in a liquid medium and reflected by a curved mirror.

FIG. 10 is a diagram illustrating a scatterometer ray trace for light scattered by a particle and collected using a second surface curved mirror 1004. In the example of FIG. 10, light reflected through an angle of 60° by the reflective surface of mirror 1004 corresponds to light scattered through an angle of 90° by object 1002. The scattered light 1008 passes by beam stop 1006, which is configured to reflect the high intensity light traveling along the beam axis. Scattered light can then be incident on a detector surface 1010, such as a CCD or a 2-D camera array as described above.

Figure 11:
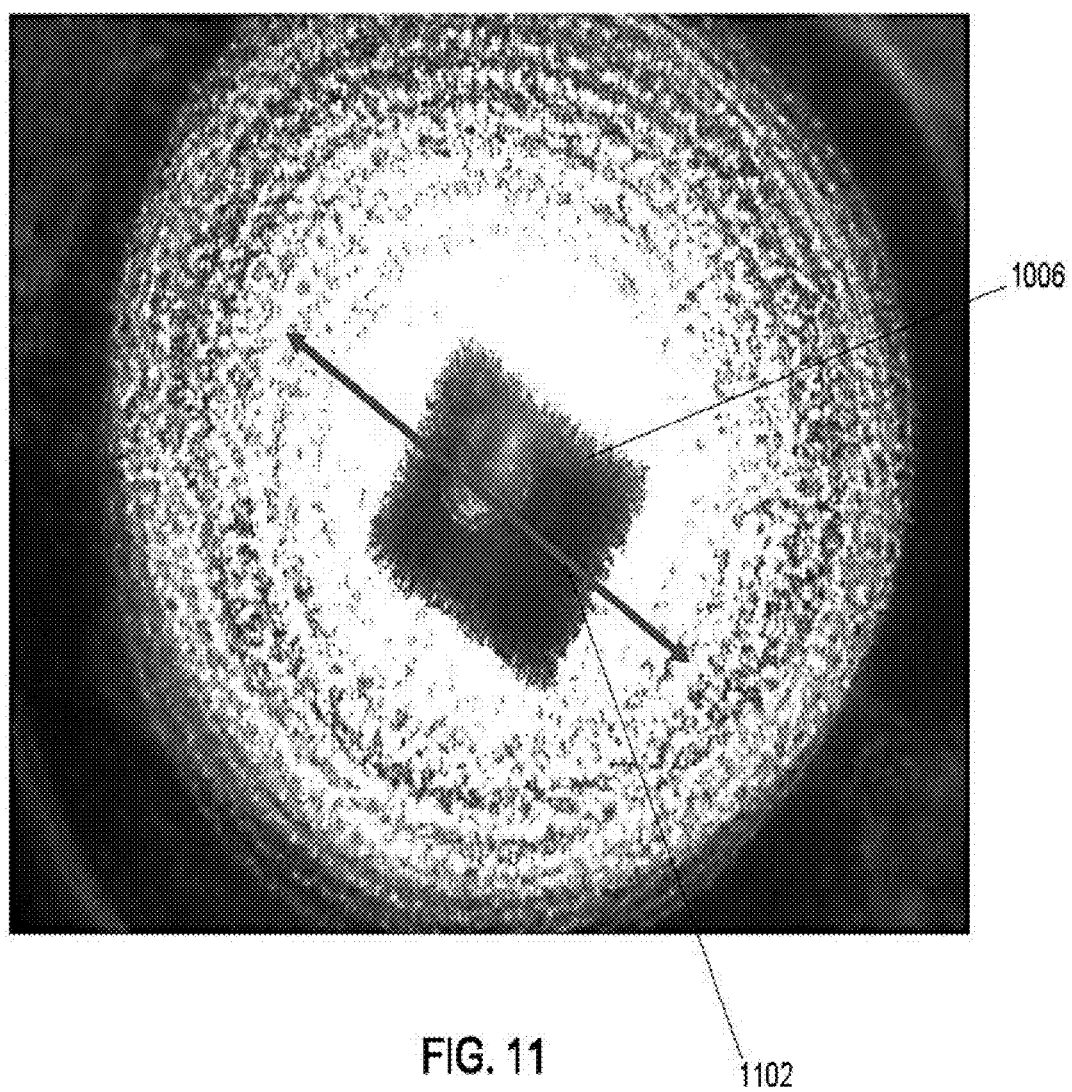
FIG. 11 is a diagram illustrating the scattered light pattern produced by the particle of FIG. 10.

FIG. 11 is a diagram illustrating a pattern produced by scattered light 1008 incident on detector 1010. The pattern depicted in FIG. 11 corresponds to the diffraction pattern generated by a sphere comprising a diameter of approximately 8 microns. Line 1102 is drawn along the laser polarization axis. Beam stop 1006 reflects light along the beam axis.

Figure 12:
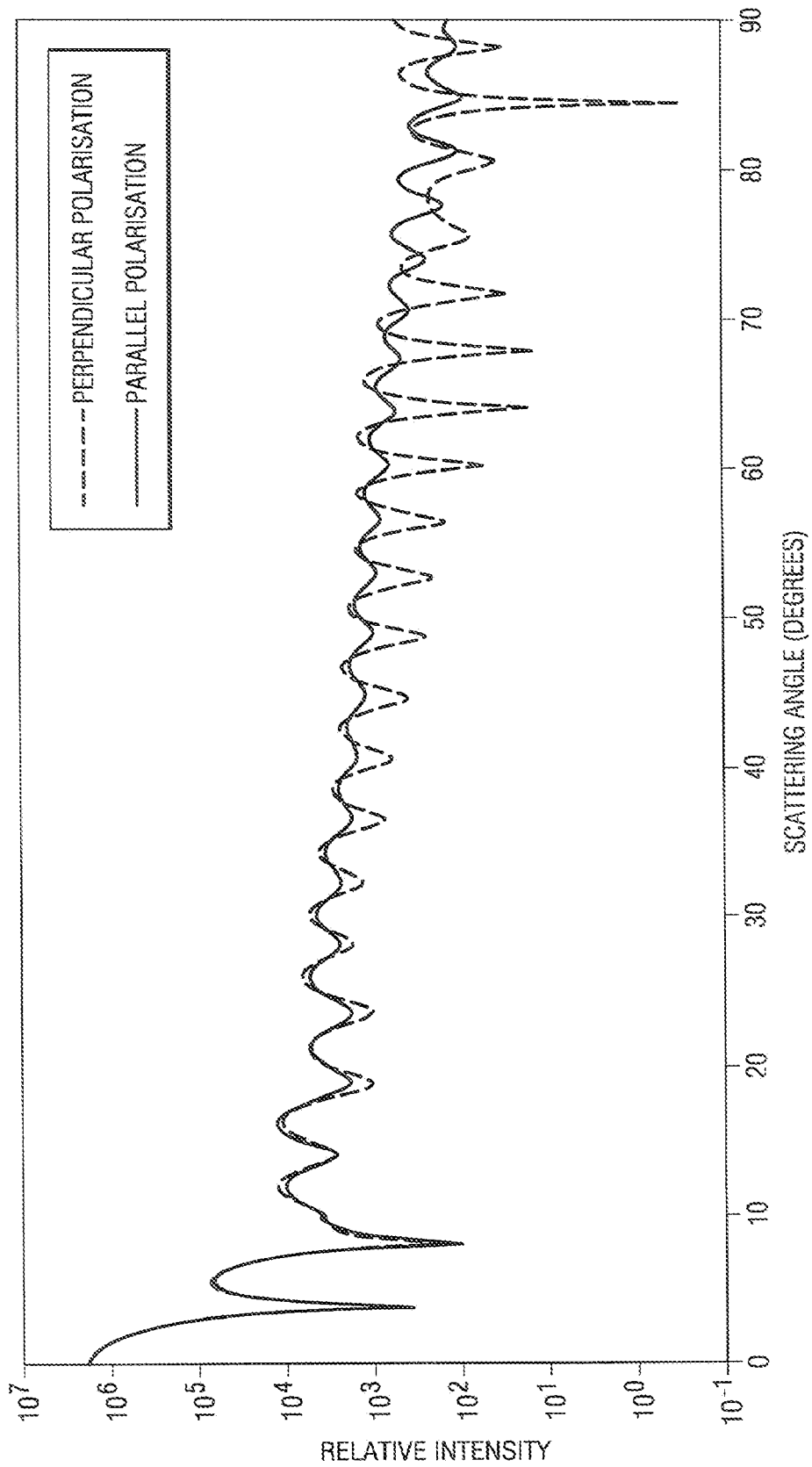
FIG. 12 is a graph illustrating the relative intensity of the scattered light versus the scattering angle.

FIG. 12 is a graph illustrating the relative intensity of scattered light versus the scatter angle for the pattern of FIG. 11. As can be seen, light scattered through an angle of 90° can be detected using optic 1004.

Thus, for example, a reflective optic, such as optic 1004 can be included in systems such as systems 100 and 200. An optic such as optic 1004 can be included in place of, or in addition to other optics with in the system. This can increase the angle 8 through which scattered light can be collected and detected. Although, systems 100 and 200 are just examples of the types of systems that can make use of a second surface curved mirror for collecting and detecting high-angle scattered light as describe above. Accordingly the embodiments described with respect to FIGS. 10-12 should not be seen as limited to implementation in systems such as systems 100 and 200.

Figure 13:
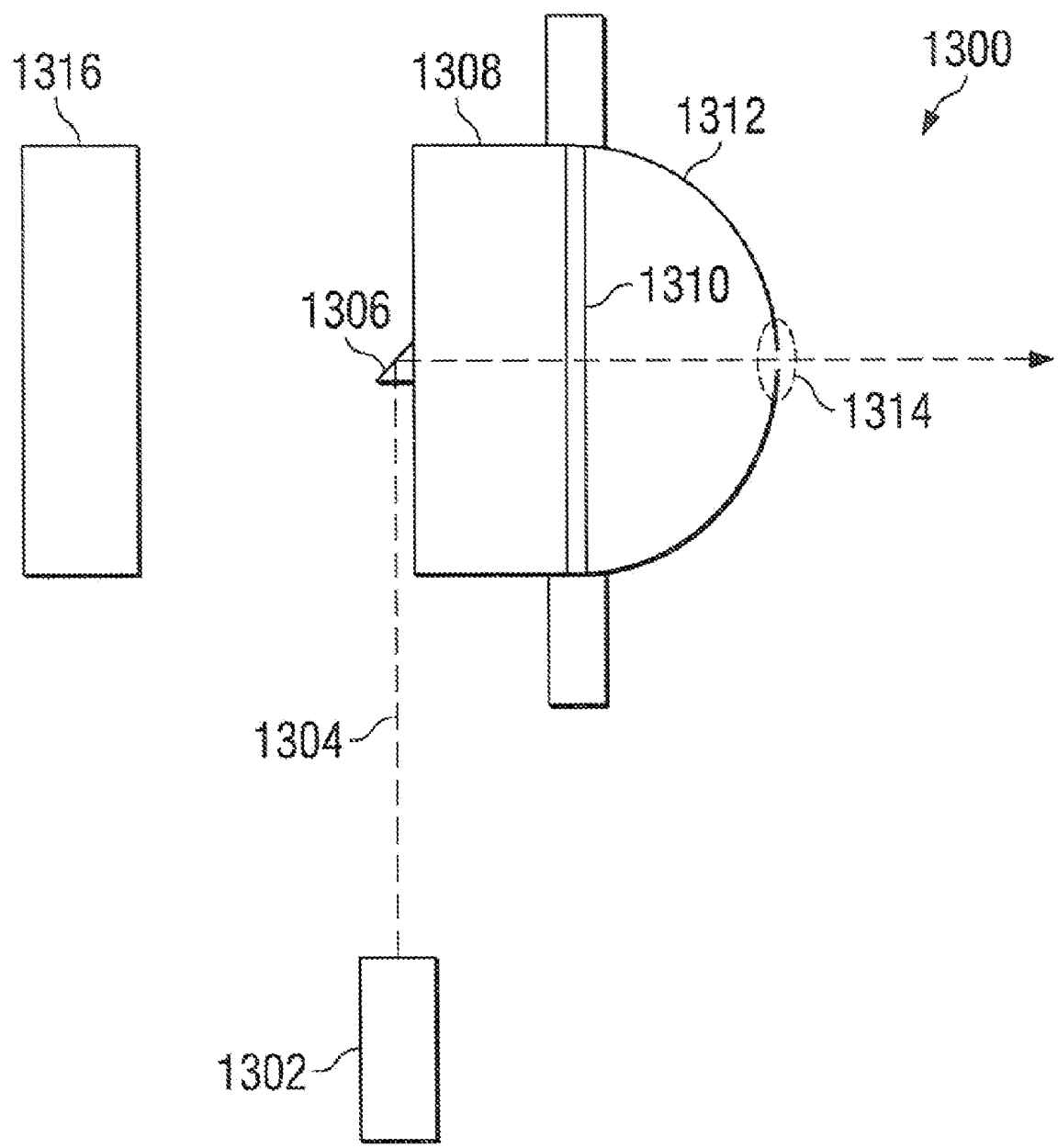
FIG. 13 is a diagram illustrating a system configured to collect light scattered by a particle and reflected by a curved reflective optic as described herein.

For example, FIG. 13 is a diagram illustrating a system 1300 configured to collect light scattered by a particle and reflected by a curved reflective optic as described above. System 1300 comprises a laser 1302 configured to generate a laser beam 1304. Beam 1304 can be directed at a 45 degree reflective silver prism 1306, which can cause beam 1304 to go through interface optic 1308, flow cell 1310, and reflective optic 1312 through unsilvered area 1314 on reflective optic 1312. Thus, silver prism 1306 and unsilvered area 1314 on reflective optic 1312 allow beam 1304 to be removed from the desired signal, much as beamstop 1006 (see FIG. 10) does in alternative embodiments.

Interface optical element 1308 can be a separate element optically coupled to flow cell 1310 with a coupling medium, or integral to the design of the flow cell 1310. Reflective optical element 1312 can also be a separate element optically coupled to flowcell 1310 with a coupling medium or integral to flowcell 1310. The scattered radiation pattern produced by an object in flowcell 1310 is reflected by reflective optical element 1312. The reflected light then falls on the 2-dimensional photo detector array 1316.

Figure 14:
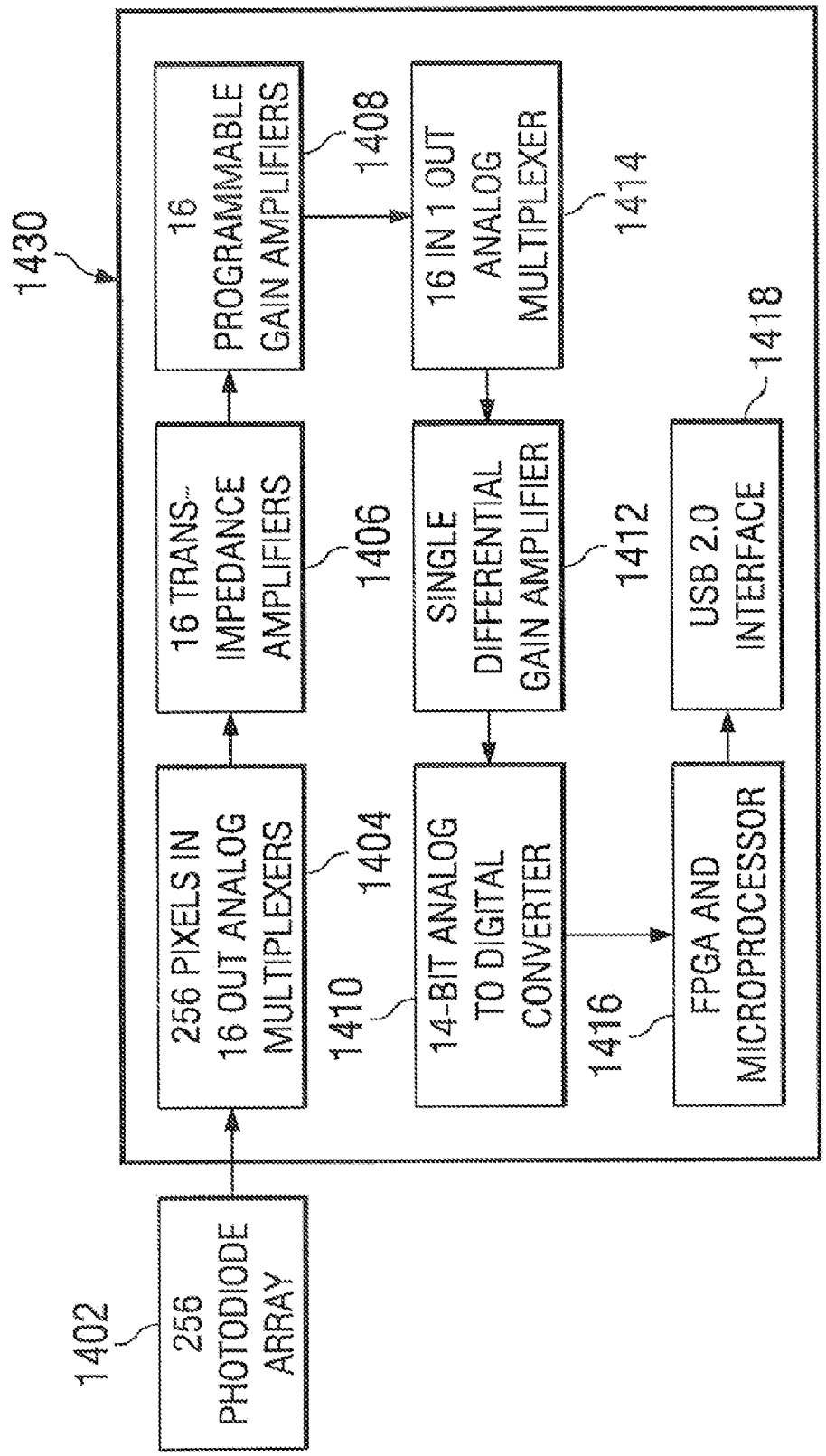
FIG. 14 is a diagram illustrating an example detector system, such as a 2-dimensional photodetector camera.

FIG. 14 is a diagram illustrating an example detector system 1400, such as detector 212 or a system including array 1316. In the example of FIG. 14, system 1400 comprises a 256-pixel detector packaged array 1402 removably attached to a signal conditioning and digitizing board 1430. Board 1430 can comprise signal conditioning amplifiers 1406, 1408 and 1412, multiplex analog switches 1404 and 1414, a 14-bit Analog to Digital Converter (ADC) 1410, a microcontroller 1418, and a USB2.0 communications chip 1418. Thus, such a system 1400 can be packaged as a complete high-speed USB 2.0 camera operating at frame rates of 1,000 frames per second upwards to 10,000 frames per second. Normally each pixel (photodiode) is connected directly to a trans-impedance amplifier 1406. A unique aspect of the disclosed 2-D camera technique is that only 16 total trans-impedance amplifiers (1406) are required to operate the entire photodiode array 1402 instead of 256 trans-impedance amplifiers, as is required in conventional designs. By using a low-noise analog multiplexer (MUX) directly to select one of 16 pixels to send to one of the trans-impedance amplifiers 1406, only 16 MUXs are required along with only 16 trans-impedance amplifiers 1406.

While the invention has been described with respect to a limited number of embodiments, the specific features of one embodiment should not be attributed to other embodiments of the invention. No single embodiment is representative of all aspects of the inventions. Moreover, variations and modifications therefrom exist. For example, the magnetic memory devices and methods of storing data described herein can be used in any circuit using circuit design tools. In some embodiments, the devices are substantially free or essential free of any feature on specifically enumerated herein. Some embodiments of the method described herein consist of or consist essentially of the enumerated steps. The appended claims intend to cover all such variations and modifications as falling within the scope of the invention.

What is claimed:

1. A system for detecting and identifying a particle in a liquid, the system comprising:
    a tubular flow cell configured to carry a liquid medium, the flow cell comprising a target zone within the liquid medium, the particle carried into the target zone by the liquid medium;

a light source configured to generate a light beam and to direct the light beam through flow cell and into the target zone;

an optic configured to collect and reflect light scattered by a particle in the target zone, the optic comprising a reflective optic having a curved reflecting surface, the reflective optic optically coupled with the flow cell, the reflective optic is also configured to collect and reflect light scattered by a particle in the liquid medium in the target zone; and a 2-dimensional detector camera configured to detect the reflected light.

2. The system of claim 1, wherein the 2-dimensional detector camera provides a frame rate from about 1000 frames per second to 10000 frames per second.

3. The system of claim 1, wherein the 2-dimensional detector camera comprises a square array of photodiodes.

4. The system of claim 3, wherein the square array of photodiodes comprises 256 active elements arranged in a 16×16 square grid.

5. The system of claim 4, wherein each of the 256 active elements comprises a size of approximately 1.1 mm$^2$.

6. The system of claim 5, wherein the 256 active elements comprise a layout having about 1.5 mm center-to-center spacing between elements.

7. The system of claim 3, wherein the 2-dimensional detector camera further comprises a signal conditioning and digitizing board connected to the array of photodiodes.

8. The system of claim 7, wherein the board comprises a plurality of trans-impedance amplifiers, wherein a plurality of photodiodes are connected to each trans-impedance amplifier.

9. The system of claim 8, wherein each of the pluralities of photodiodes are connected to their respective trans-impedance amplifier via a multiplexer.

10. The system of claim 1, wherein the reflective optic is a second surface curved mirror.

11. The system of claim 10, wherein the reflective optic allows light scattered through an angle of 90° with respect to the curved reflecting surface of the reflective optic to be captured by the detector.

12. The system of claim 1, further comprising a beam stop configured to deflect the light beam after it has passed through the target zone.

13. A system for detecting and identifying a particle in a liquid, the system comprising:
a tubular flow cell comprising a flowing liquid media and a target zone, the particle carried in the path of a light beam by the liquid media;
a light source configured to generate the light beam and direct the light beam through the flow cell and into the target zone;
an interface optic;
a reflective optic configured to collect and reflect light scattered by a particle carried by the liquid media through the target zone, the optic comprising a reflective optic having a curved reflecting surface, the reflective optic is integral to the flow cell and the reflective optic optically coupled with the liquid medium in the target zone, the reflective optic configured to collect and reflect light scattered by a particle in the liquid medium in the target zone; and
a 2-dimensional detector camera configured to detect the reflected light.

14. The system of claim 13, wherein the 2-dimensional detector camera provides a frame rate from about 1000 frames per second to 10000 frames per second.

15. The system of claim 13, wherein the 2-dimensional detector camera comprises a square array of photodiodes.

16. The system of claim 13, wherein the interface optic is integral to the flow cell.

17. The system of claim 13, wherein the reflective optic is integral to the flowcell.

18. The system of claim 13, further comprising a beam stop configured to deflect the light beam after it has passed through the target zone.

19. A system for detecting and identifying a particle in a liquid, the system comprising:
a tubular flow cell configured to carry a liquid medium, the flow cell comprising a target zone within the liquid medium, the particle carried into the target zone by the liquid medium;
a light source configured to generate a light beam and to direct the light beam through the flow cell and into the target zone;
an optic configured to collect and reflect light scattered by a particle in the target zone, the optic comprising a reflective optic having a curved reflecting surface, the reflective optic being integral to and optically coupled with the flow cell and wherein the reflective optic is also configured to collect and reflect light scattered by a particle in the liquid medium in the target zone; and
a 2-dimensional detector camera configured to detect the reflected light.

20. The system of claim 19, wherein the 2-dimensional detector camera provides a frame rate from about 1000 frames per second to 10000 frames per second.

21. The system of claim 19, wherein the 2-dimensional detector camera comprises a square array of photodiodes.

22. The system of claim 21, wherein the square array of photodiodes comprises 256 active elements arranged in a 16×16 square grid.

23. The system of claim 22, wherein each of the 256 active elements comprises a size of approximately 1.1 mm$^2$.

24. The system of claim 23, wherein the 256 active elements comprise a layout having about 1.5 mm center-to-center spacing between elements.

25. The system of claim 21, wherein the 2-dimensional detector camera further comprises a signal conditioning and digitizing board connected to the array of photodiodes.

26. The system of claim 25, wherein the board comprises a plurality of trans-impedance amplifiers, wherein a plurality of photodiodes are connected to each trans-impedance amplifier.

27. The system of claim 26, wherein each of the pluralities of photodiodes are connected to their respective trans-impedance amplifier via a multiplexer.

28. The system of claim 19, wherein the reflective optic is a second surface curved mirror.

29. The system of claim 28, wherein the reflective optic allows light scattered through an angle of 90° with respect to the curved reflecting surface of the reflective optic to be captured by the detector.

30. The system of claim 19, further comprising a beam stop configured to deflect the light beam after it has passed through the target zone.

* * * * *